(12) United States Patent
Spahn

(10) Patent No.: US 7,266,177 B2
(45) Date of Patent: Sep. 4, 2007

(54) METHOD AND DEVICE FOR GENERATING AN X-RAY IMAGE

(75) Inventor: Martin Spahn, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/408,257

(22) Filed: Apr. 20, 2006

(65) Prior Publication Data

US 2006/0245546 A1  Nov. 2, 2006

(30) Foreign Application Priority Data

Apr. 20, 2005 (DE) ...................... 10 2005 018 341

(51) Int. Cl.
*H05G 1/44* (2006.01)

(52) U.S. Cl. ........................................ 378/108; 378/97

(58) Field of Classification Search ................. 378/96, 378/97, 108, 4, 19, 62, 98.8
See application file for complete search history.

(56) References Cited

U.S. PATENT DOCUMENTS 5,448,613 A     9/1995  Haendle et al. ............ 378/98.7
6,594,339 B1 *  7/2003  Alving et al. ............... 378/98.7

OTHER PUBLICATIONS

M. Spahn, V. Heer and R. Freytag, "Flachbilddetektoren in der Röntgendiagnostik", ("Flat-panel dectectors in x-ray diagnostics", Der Radiologe (The Radiologist) 43, 2003, pp. 340-350.

* cited by examiner

*Primary Examiner*—Courtney Thomas

(57) ABSTRACT

The invention relates to a method for generating an x-ray image. In order to minimize the dose rate the invention proposes that the body to be examined is first irradiated with a first dose rate. On the basis of first signals measured during this process, a second dose rate required for generating the x-ray image is calculated and parameters are determined which are used to subsequently operate the x-ray tube automatically in order to deliver the second dose rate.

14 Claims, 3 Drawing Sheets

METHOD AND DEVICE FOR GENERATING AN X-RAY IMAGE

CROSS REFERENCE TO RELATED APPLICATIONS

This application claims priority to the German Application No. 10 2005 018 341.7, filed Apr. 20, 2005 which is incorporated by reference herein in its entirety.

FIELD OF INVENTION

The invention relates to a method and a device for generating an x-ray image whilst using the lowest possible dose rate.

BACKGROUND OF INVENTION

On the basis of the prior art, ionization chambers located upstream of the detector are used for setting the dose rate. Particularly in the case of digital systems, such types of ionization chambers may under certain circumstances appear on the x-ray image which is generated. Although such undesired imaging can be counteracted by means of suitable calibration, such calibration operations do however in turn result in undesired artifacts.

SUMMARY OF INVENTION

Apart from this, external ionization chambers need to be separately synchronized, in other words they must be activated at the time when the detector is ready to capture an image and an x-ray pulse is generated by the x-ray source. Finally, the provision of an ionization chamber upstream of the detector contributes to an increase in the overall height of the system.

An x-ray diagnostics installation having an x-ray image intensifier and a semiconductor detector is known from U.S. Pat. No. 5,448,613. In order to detect the image brightness, a group of detector elements is connected to a readout circuit comprising an integration stage while the semiconductor detector is being irradiated with x-ray radiation. This therefore brings about a summation of the measured signals. The output signal from the integration stage is fed to a threshold circuit and compared with a threshold. If the threshold is exceeded, the threshold circuit delivers an output signal which causes a high-voltage generator to be switched off.

An object of the invention is to eliminate the disadvantages originating from the prior art. It should in particular specify a method and a device for generating an x-ray image whilst using the lowest possible dose rate.

This object is achieved by the claims. Advantageous embodiments of the invention will emerge from the dependent claims.

According to the invention, a method for generating an x-ray image comprising the following steps is provided:
- provision of an x-ray source and a semiconductor detector comprising a large number of detector elements arranged opposite the source,
- irradiation of a body to be examined with x-ray radiation of a predefined dose rate during a first time interval,
- measurement of first signals using at least one section of the detector elements,
- calculation of a second dose rate required for generating the x-ray image and determination of at least one parameter for setting the x-ray source in order to deliver the second dose rate,
- irradiation of the body to be examined with the second dose rate generated by using the parameter during a second time interval and
- measurement of second signals using the semiconductor detector and generation of an x-ray image reproducing the measured second signals.

By using the proposed method it is possible to dispense with the provision of an ionization chamber. The second dose rate required for producing the x-ray image is determined prior to generation of the x-ray image by first irradiating the body to be examined with x-ray radiation of a predefined dose rate during a first time interval. In this situation, the patient is merely subjected to a low first dose rate. The first dose rate is however sufficient for calculating the second dose rate and thus for determining at least one parameter which is used to set the x-ray source such that it enables precisely the second dose rate to be delivered. The actual x-ray image capture then takes place using the second dose rate generated by using the parameter. From the second signals measured using the semiconductor detector an x-ray image is then generated in a conventional manner.

The expression "second dose rate" is understood to be a dose rate which is as low as possible but which enables the generation of a perfect x-ray image within the dynamic range predefined by the semiconductor detector.

According to an advantageous embodiment of the invention, provision is made whereby a predefined geometric arrangement of one section of the detector elements is used in order to measure the first signals. Only certain rows of detector elements in the semiconductor detector spaced at a predefined distance from one another can be used, for example. Likewise, it is possible for the geometric arrangement to correspond to the outlines of rectangles or circles. Crossed lines or combinations of rectangles, circles and crossed lines are also possible. In addition, it is possible to connect together a plurality of adjacent detector elements such that larger surface area elements are produced.

According to a further advantageous embodiment, provision is made whereby the section of the detector elements is less than 20% of the total number of detector elements in the semiconductor detector. Due to the fact that only one section of the detector elements is used for measuring the first signals, the determination of the parameter can take place particularly quickly. As a result, the first time interval is normally shorter than the second time interval.

According to an advantageous embodiment, the parameter is selected from the following group: cathode current strength, amplitude of an acceleration voltage, type of a filter, duration of the second time interval. The parameter or parameters to be set thus pertain particularly to the setting of a high-voltage generator for the operation of an x-ray tube. It is naturally also possible for a plurality of the aforementioned parameters to be calculated with regard to an optimized second dose rate and to be used for generating the x-ray radiation.

According to a further embodiment, provision is made whereby a third time interval separating the first time interval from the second time interval has its length determined by the time required in order to calculate the parameter. In practice, the third time interval is extremely short, dependent on the high computing power of a computer advantageously used for calculation purposes. As a consequence, the body to be examined can also be irradiated with the first dose rate during the third time interval. This does not result in any significant additional burden on the patient.

According to a further embodiment, the second dose rate is greater than the first dose rate. It serves to generate the x-ray image reproducing the measured second signals.

Further according to the invention, a device for generating an x-ray image is provided, having

- an x-ray source and a semiconductor detector comprising a large number of detector elements arranged opposite the source,
- a facility for irradiating a body to be examined with x-ray radiation of a predefined first dose rate during a first time interval,
- a facility for calculating a second dose rate required for generating the x-ray image and determining at least one parameter for setting the x-ray source in order to deliver the second dose rate,
- a facility for irradiating the body to be examined with the second dose rate during a second time interval and
- a facility for generating an x-ray image reproducing measured second signals.

With regard to the proposed device, this can be a conventional device which can be controlled by means of a computer. The software required in order to operate the device in accordance with the method according to the invention is characterized in particular by the fact that the body to be examined is thus irradiated in an automated fashion in a two-stage process at least during the generation of a first x-ray image. In the first stage the body to be examined is irradiated with x-ray radiation of a first dose rate during a first time interval. In this situation, the first dose rate and/or the first time interval are preferably predetermined. These may be variables which can be set in the software. In addition, a facility can be provided for calculating a second dose rate from first signals measured using at least one section of the detector elements. The section of the detector elements and its geometric arrangement can similarly be predefined or selected on the software side. The first signals thus measured can be processed by using suitable algorithms and the optimum second dose rate required in order to produce an x-ray image can be calculated or extracted therefrom. At least one parameter, in particular for controlling a high-voltage generator for operation of an x-ray source, can in turn be determined from the second dose rate. In the second stage, using the calculated parameter, x-ray radiation is then generated with the second dose rate and the x-ray image is produced on the basis of the second signals which thus result.

Regarding the advantageous embodiments of the device, reference should be made to the advantageous embodiments described in relation to the method, which by analogy also constitute advantageous features of the device.

BRIEF DESCRIPTION OF THE DRAWINGS

The invention will be described in detail in the following with reference to the drawings. In the drawings.

DETAILED DESCRIPTION OF INVENTION

Figure 1:
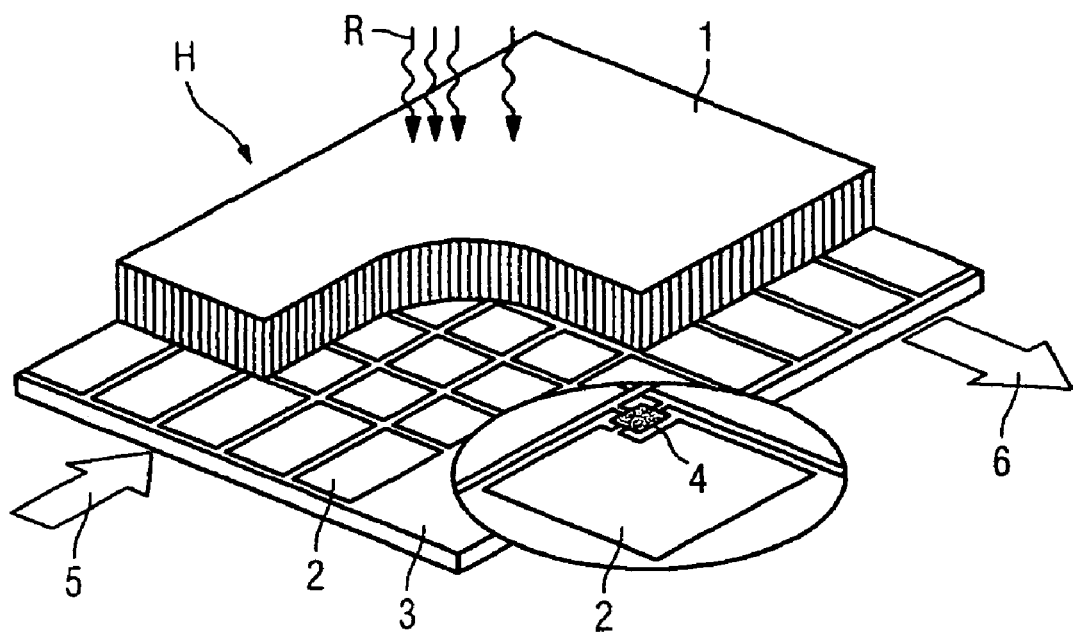
FIG. 1 shows a perspective view of a semiconductor detector according to the prior art.

FIG. 1 shows a perspective view of a known semiconductor detector according to the prior art. With regard to the semiconductor detector H shown, a converter layer 1 is applied on a readout matrix 3 provided with a large number of detector elements 2. Each of the detector elements 2 can have a switch 4 which can be used to switch it on or off by means of a control electronics unit 5 which is merely indicated schematically here. The reference character 6 likewise schematically denotes a readout electronics unit.

With regard to the semiconductor detector H shown here, x-ray radiation R incident upon the converter layer 1 is converted into light. The light is captured in the form of charge signals by means of the detector elements 2 which here take the form of photodiodes. To this end, the detector elements 2 can be switched on and off row by row, for example, by means of the control electronics unit 5. The charge signals from the detector elements 2 can then likewise be read out row by row, for example, by means of the readout electronics unit 6.

The present invention is by no means restricted to the semiconductor detector H shown by way of example in FIG. 1. It is also suitable in combination with other semiconductor detectors in which, for example, instead of the converter layer 1 a direct converter is provided which converts incident x-ray radiation R directly into charge signals. Such a direct converter can be manufactured from selenium, for example. In addition, semiconductor detectors with CCDs (charge coupled devices), APS (active pixel sensor) or large-area CMOS chips can be used. Reference is made in this context to the publication Spahn et al., Flachbilddetektoren in der Röntgendiagnostik [Flat-panel detectors in x-ray diagnostics], Der Radiologe [The Radiologist] 43 (2003), pp. 340 to 350, whose disclosure is hereby incorporated.

Figure 2:
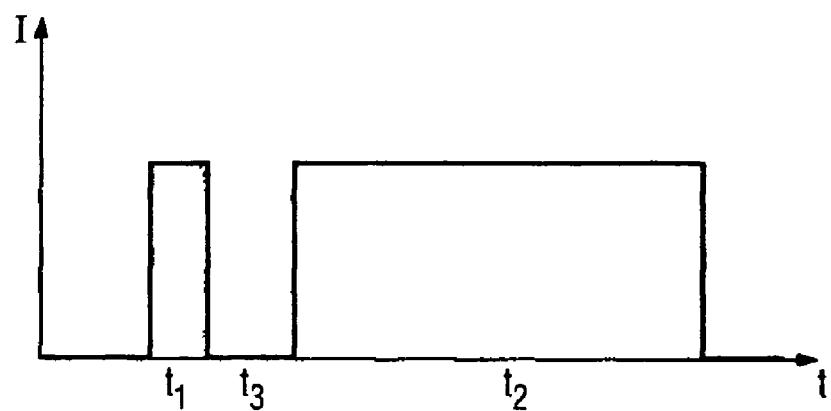
FIG. 2 shows the waveform according to the invention for the cathode current as a function of the time.

FIG. 2 shows a waveform for the cathode current I as a function of the time typically occurring during execution of the method according to the invention. The cathode current I is turned on at the beginning of a first time interval $t_1$. At the same time a predefined high voltage is applied between a cathode and an anode of an x-ray source. As a consequence, a body to be examined is irradiated with x-ray radiation R at a first dose rate. At the end of the first time interval $t_1$ the cathode current I is turned off. In a third time interval $t_3$ which now follows, a calculation of a second dose rate required in order to produce an x-ray image takes place on the basis of measured first signals and a predefined algorithm. During the calculation of the second dose rate a dynamic range of the semiconductor detector H is taken into consideration as a limit condition. Within the dynamic range, a minimum second dose rate for generating the x-ray image is calculated. One or more parameters for controlling the x-ray source are determined on the basis of the calculated second dose rate. With regard to the parameters, these can for example be the strength of the cathode current I, the amplitude of an x-ray voltage, the provision or non-provision of a filter and also the duration of the second time interval $t_2$. The parameter or parameters calculated are passed to a control program and the x-ray source is then put into operation again for a second time interval $t_2$. As can be seen from FIG. 2, the cathode current I is also turned on again. The cathode current I can have the same value in the first time interval $t_1$ and in the second time interval $t_2$. It can of course also be different, depending on the calculated parameters. The pre-calculated second dose rate is delivered by the x-ray source during the second time interval $t_2$.

In accordance with a variant of the method according to the invention, it is also possible that the cathode current I is not turned off during the third time interval $t_3$ but is present from the beginning of the first time interval $t_1$ through to the end of the second time interval $t_2$. Depending on the result achieved during the calculation, at the beginning of the second time interval $t_2$ it can remain unchanged or can also be increased or decreased. In addition, at the beginning of the second time interval $t_2$ an x-ray voltage can either remain the same or can also be increased or decreased. The length of the second time interval $t_2$ can also be changed in order to achieve the desired second dose rate.

Figure 3:
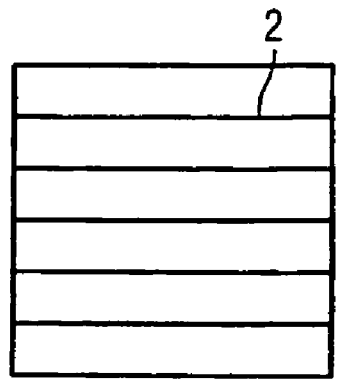
FIG. 3 shows a first embodiment of a geometric arrangement of detector elements selected for the measurement of first signals.
Figure 4:
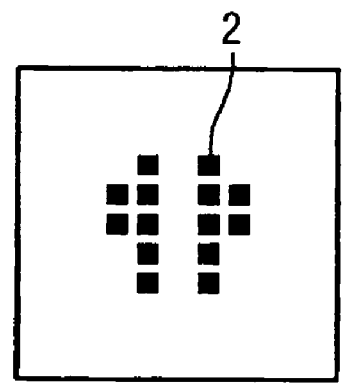
FIG. 4 shows a second embodiment of the geometric arrangement of detector elements selected for the measurement of first signals and FIG. 5 shows a flowchart.

FIGS. 3 and 4 show schematic top views of different geometric arrangements of the section of the detector elements 2, which are used for the measurement of the first signals. The selected detector elements 2 can be rows which are spaced at a distance from one another. They can also be arranged in the form of a cross or, for example, in the geometric arrangements which can be seen in FIG. 4. The geometric arrangement of the detector elements 2 selected for the measurement of the first signals can be set under program control, depending on an organ to be examined for example. In order to set a suitable geometry it is possible for example to extract data from a radiology information system (RIS). By using only a section of the detector elements 2 in a predefined geometric arrangement for the measurement of the first signals, the step for calculating the second dose rate required in order to produce the x-ray image and also the parameter or parameters can be performed at a high speed.

Figure 5:
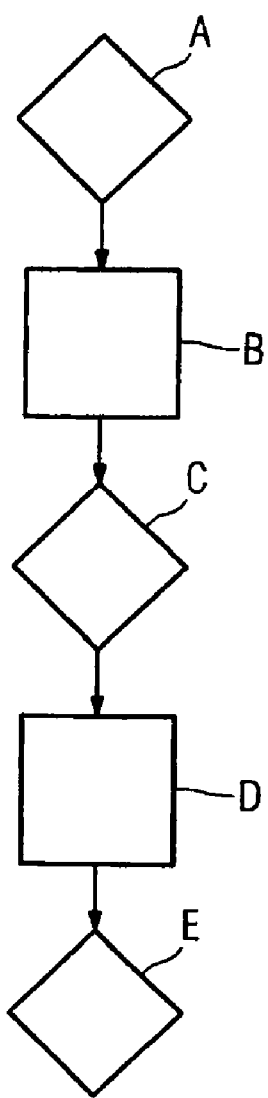

FIG. 5 shows the essential steps of the method according to the invention in their temporal sequence in a flowchart. During a first step A, a so-called "analysis shot" is fired, in other words a body to be examined is irradiated during a predefined first time interval $t_1$ with a predefined first dose rate. Then in a second step B the first signals thus measured are read out from a predefined section of detector elements 2 and conveyed to a computer. Using the computer, in a third step C a second dose rate and a parameter set suitable for generating the second dose rate are calculated for operation of an x-ray source. The algorithms used for the calculation are such that the second dose rate is as low as possible. The second dose rate is however chosen such that second signals can thus be measured within a predefined dynamic range of the semiconductor detector H and that a meaningful x-ray image can thus be generated.

During a fourth step D, the body to be examined is irradiated with the second dose rate, using the calculated parameter set. Second signals are measured by means of the semiconductor detector H.

In a fifth step E, the second signals are finally read out and processed to produce an x-ray image.

Steps A to C may also be omitted in the case of subsequent x-ray imaging operations provided there is no change in the position of the body to be examined or an area to be examined on the body to be examined.

Figure 6:
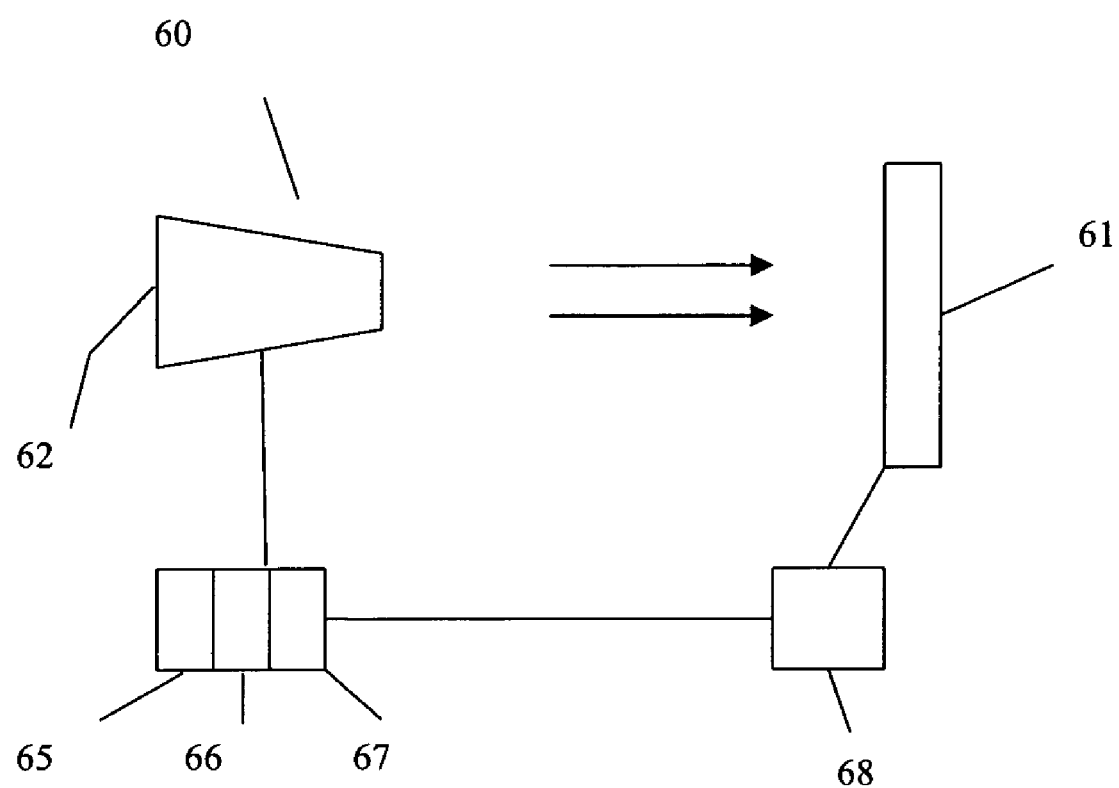
FIG. 6 shows an x-ray image device according to one embodiment.

FIG. 6 illustrates a device for generating an x-ray image 60. The device 60 comprises an x-ray source 62; a semiconductor detector 61 comprising a plurality of detector elements (e.g., item 2 in FIG. 1 described above) and arranged opposite the x-ray source 62. The device 60 comprises a first device unit 65 for irradiating a body under examination with x-rays originating from the x-ray source and having a prescribed first dose rate, the first dose rate applied during a first time interval, and for acquiring a first plurality of image signals by at least one part of the detector elements. The device 60 also comprises a processing device 68 for calculating a second dose rate required for generating an x-ray image, the calculation based on the acquired first plurality of signals, and for determining at least one setting parameter for adjusting the x-ray source to emit the calculated second dose rate. Also included with the device 60 is a second device unit 66 for irradiating the body with the second dose rate during a second time interval, and for acquiring a second plurality of image signals by the semiconductor detector; and a third device unit 67 for generating the x-ray image from the acquired second plurality of image signals.

The invention claimed is:

1. A method of generating an x-ray image, comprising:
providing an x-ray source;
providing a semiconductor detector comprising a plurality of detector elements and arranged opposite the x-ray source;
irradiating a body under examination with x-rays originating from the x-ray source having a prescribed first dose rate, the first dose rate applied during a first time interval;
acquiring a first plurality of image signals by at least one part of the detector elements; wherein the at least one part of the detector elements has a prescribed geometric arrangement of the respective detector elements; said prescribed geometric arrangement comprising an outline of a rectangle or circle, or a crossed line, or a combination thereof;
calculating a second dose rate required for generating an x-ray image, the calculation based on the acquired first plurality of signals;
determining at least one setting parameter for adjusting the x-ray source to emit the calculated second dose rate;
irradiating the body with x-rays originating from the x-ray source and having the second dose rate, the second dose rate generated by the x-ray source set to the setting parameter and applied during a second time interval;
acquiring a second plurality of image signals by the semiconductor detector; and
generating the x-ray image from the acquired second plurality of image signals.

2. The method according to claim 1, wherein the at least one part of the detector elements has less than 20% of a total number of the detector elements.

3. The method according to claim 1, wherein the first time interval is shorter than the second time interval.

4. The method according to claim 1, wherein the setting parameter is selected from the group consisting of a cathode current amperage, an amplitude of an acceleration voltage, a filter type applied to the x-rays and a duration of the second time interval.

5. The method according to claim 1, wherein the first and second time intervals are separated by a third time interval, a duration of the third time interval determined from a calculation time necessary for calculating the setting parameter.

6. The method according to claim 5, further comprising irradiating the body with the first dose rate during the third time interval.

7. The method according to claim 1, wherein the second dose rate is bigger than the first dose rate.

8. A device for generating an x-ray image, comprising:
an x-ray source;
a semiconductor detector comprising a plurality of detector elements and arranged opposite the x-ray source;

a first device unit for irradiating a body under examination with x-rays originating from the x-ray source and having a prescribed first dose rate, the first dose rate applied during a first time interval, and for acquiring a first plurality of image signals by at least one part of the detector elements according to a prescribed geometric arrangement of the respective detector elements: wherein said prescribed geometric arrangement comprises an outline of a rectangle or a circle, or a crossed line, or a combination thereof;

a processing device for calculating a second dose rate required for generating an x-ray image, the calculation based on the acquired first plurality of signals, and for determining at least one setting parameter for adjusting the x-ray source to emit the calculated second dose rate;

a second device unit for irradiating the body with the second dose rate during a second time interval, and for acquiring a second plurality of image signals by the semiconductor detector; and a third device unit for generating the x-ray image from the acquired second plurality of image signals.

9. The device according to claim 8, wherein the at least one part of the detector elements has less than 20% of a total number of the detector elements.

10. The device according to claim 8, wherein the first time interval is shorter than the second time interval.

11. The device according to claim 8, wherein the setting parameter is selected from the group consisting of a cathode current amperage, an amplitude of an acceleration voltage, a filter type applied to the x-rays and a duration of the second time interval.

12. The device according to claim 8, wherein the first and second time intervals are separated by a third time interval, a duration of the third time interval determined from a calculation time necessary for calculating the setting parameter.

13. The device according to claim 12, wherein the body is irradiated with the first dose rate during the third time interval.

14. The device according to claim 8, wherein the second dose rate is bigger than the first dose rate.

* * * * *